(12) United States Patent
Patterson

(10) Patent No.: US 10,737,080 B2
(45) Date of Patent: Aug. 11, 2020

(54) SCALP TREATMENT TOOL

(71) Applicant: Miisha Patterson, Denver, CO (US)

(72) Inventor: Miisha Patterson, Denver, CO (US)

(*) Notice: Subject to any disclaimer, the term of this patent is extended or adjusted under 35 U.S.C. 154(b) by 573 days.

(21) Appl. No.: 15/158,372

(22) Filed: May 18, 2016

(65) Prior Publication Data

US 2016/0339221 A1    Nov. 24, 2016

Related U.S. Application Data

(60) Provisional application No. 62/163,499, filed on May 19, 2015.

(51) Int. Cl.
*A61H 1/00* (2006.01)
*A61M 35/00* (2006.01)
*A61H 7/00* (2006.01)
*A61H 15/00* (2006.01)

(52) U.S. Cl.
CPC ........... *A61M 35/003* (2013.01); *A61H 7/003* (2013.01); *A61H 2015/0064* (2013.01); *A61H 2201/105* (2013.01); *A61H 2205/021* (2013.01); *A61M 2210/06* (2013.01)

(58) Field of Classification Search
CPC . A61M 35/003; A61M 2210/06; A61H 7/003; A61H 2201/105; A61H 2015/0064; A61H 2205/021; A61H 15/0092; A61H 15/00; A61H 2201/0153; A45D 34/041; A45D 40/261; A45D 2200/20
See application file for complete search history.

(56) References Cited

U.S. PATENT DOCUMENTS

| | | | | |
|---|---|---|---|---|
| 2,837,756 A * | 6/1958 | Barlow | .................. | B65D 47/36 15/105 |
| 3,968,789 A * | 7/1976 | Simoncini | .............. | A46B 13/04 601/95 |
| 5,054,504 A * | 10/1991 | Winrow | .................. | A45D 19/02 132/110 |
| 2004/0097890 A1* | 5/2004 | Wilkinson | .......... | A61M 35/003 604/289 |
| 2005/0025558 A1* | 2/2005 | Severa | .................... | A45D 34/04 401/179 |
| 2006/0287616 A1* | 12/2006 | Nan | ....................... | A45D 34/041 601/17 |
| 2007/0125113 A1* | 6/2007 | Habatjou | .............. | A45D 34/041 62/293 |
| 2011/0226273 A1 | 9/2011 | Deardorff et al. | | |

(Continued)

FOREIGN PATENT DOCUMENTS

EP    1428455 A1    6/2004
EP    1452109 A1    9/2004

OTHER PUBLICATIONS

Jen Hugh Products Youtube slideshow, https://www.youtube.com/watch?v=7ppXyiOlOxs, published on Oct. 6, 2015, 4 pages.

*Primary Examiner* — Quang D Thanh
(74) *Attorney, Agent, or Firm* — Dorsey & Whitney LLP

(57) ABSTRACT

An apparatus and related method provide an effective treatment of skin itch and skin rash, primarily for the scalp. The apparatus may be utilized on the scalp of an individual applied between rows of tightly braided hair. The apparatus may apply a therapeutic treatment such as a moisturizing treatment directly to the scalp while being used to relieve the scalp of the itch.

19 Claims, 7 Drawing Sheets

(56) References Cited

U.S. PATENT DOCUMENTS

| | | | |
|---|---|---|---|
| 2011/0293354 A1* | 12/2011 | Dwyer | A45D 34/042 401/176 |
| 2013/0251440 A1* | 9/2013 | Young | A45D 34/041 401/213 |
| 2014/0119807 A1* | 5/2014 | Tarlow | B43K 23/008 401/6 |
| 2014/0358051 A1* | 12/2014 | Rowen | A61M 35/003 601/129 |
| 2017/0027302 A1* | 2/2017 | Gieux | A45D 34/041 |
| 2017/0157378 A1* | 6/2017 | Chang | A61M 35/003 |

\* cited by examiner

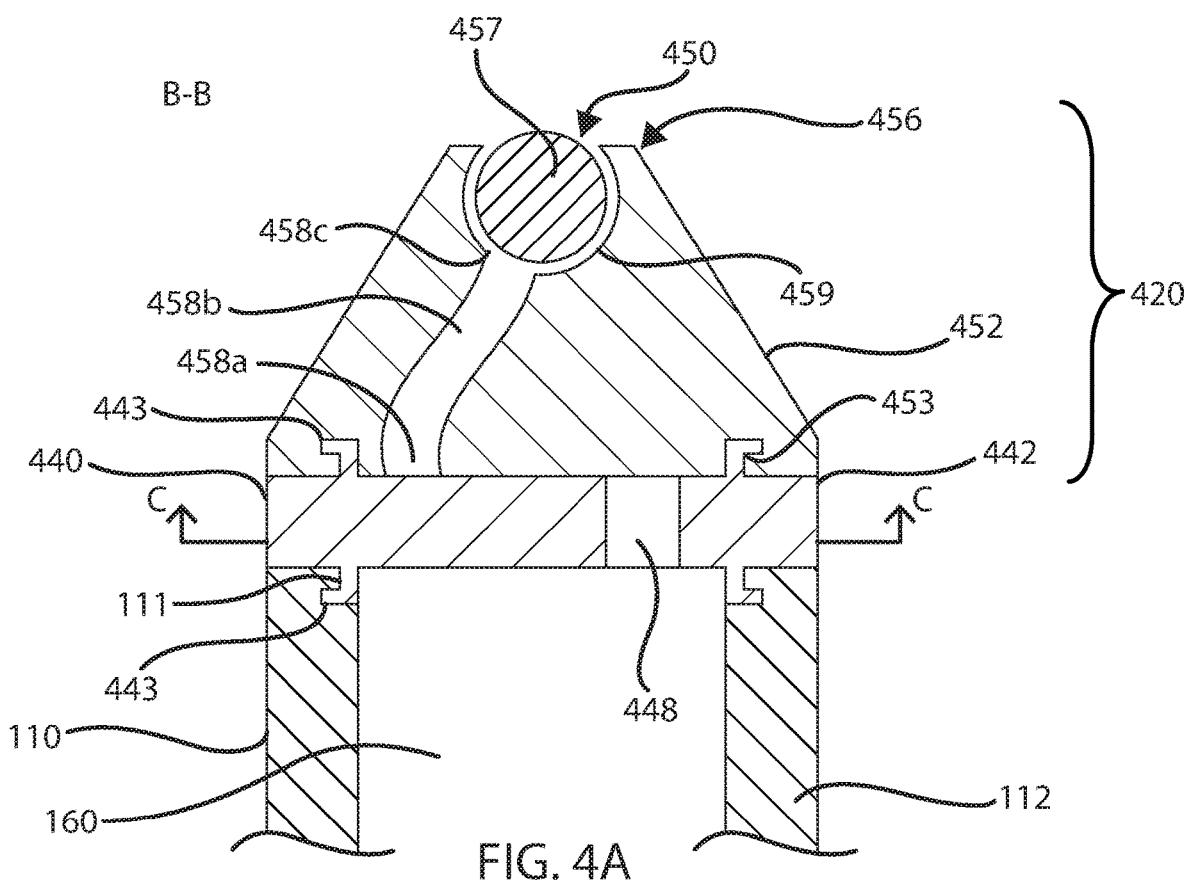
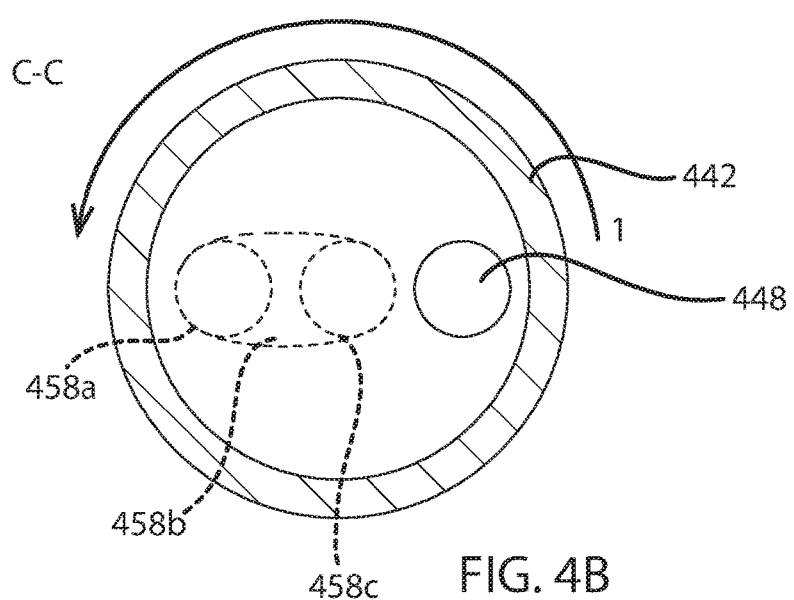

SCALP TREATMENT TOOL

CROSS REFERENCE TO RELATED APPLICATIONS

This application claims the benefit of priority pursuant to 35 U.S.C. § 119(e) of U.S. provisional application No. 62/163,499 filed 19 May 2015 entitled "Scalp treatment tool," which is hereby incorporated herein by reference in its entirety

TECHNICAL FIELD

The technology disclosed herein is related to systems and methods for treating skin, particularly the scalp, with a therapeutic scalp treatment and a mechanical treatment.

BACKGROUND

Individuals style their hair in different ways, sometimes using artificial hair, hair attachments, extensions, weaves, and wigs. The usage of these hair accessories creates various issues and problems for the user's scalps. The various issues and problems may include scalps that are itchy and dry. The scalp may become irritated which causes hair to break off. Sometimes the hair braided to the scalp is tight and it is difficult for oils and moisturizers to reach the scalp under the braid. Further, dandruff and psoriasis can be difficult to treat under such artificial hair products.

Hair weaves and hair extensions are done by braiding the wearer's natural hair flat to the head and sewing artificial hair to the braids. This is done for thickness, length, and to wear a different texture of hair. Because the hair is braided and the hair extension is sewn on, it is hard to scratch, massage, or apply treatment directly to the scalp. Various hairstyles may make it difficult for the person with that hairstyle to reach the scalp.

There are multiple reasons why a user with such an arrangement of hair might want to manipulate their scalp. For example, the scalp might get itchy or irritated. Alternatively, there might be dandruff or residue that the user would like to dislodge. To address such problems, the user might want to rub or otherwise stimulate points on the scalp, either to relieve itch and irritation or to help dislodge dandruff or residue. Alternatively, the user might want to apply a chemical treatment, such as a cleaning agent, a moisturizer, a medical treatment, or cosmetic treatment to the scalp to help care for it. Whether due to artificial hair, such as a hair weave, extension, or wig, or due to a natural hairstyle, the hair may create a barrier on or around the scalp that is difficult to penetrate.

Thus, those individuals with hair which blocks access to their scalps would like to be able to manipulate their scalps so as to be able to relieve and address these problems. Furthermore, the individuals would like to be able to manipulate their scalps without disrupting a natural hairstyle or artificial weaves or wigs. Still further, the individuals would like to apply chemical or other treatments to the scalp directly and at the same time as physically manipulating the scalp by scratching or the like.

Individuals can use elongated implements, such as a pick, pen, or pencil to attempt to reach and manipulate their scalps. However, these implements may cause damage to the scalp and fail to provide therapeutic treatment. For example, a pen would potentially mark the scalp with ink and the graphite "lead" of a pencil could potentially break off and lodge within the skin of a user' scalp. Current technology is not well adapted to care for a user's scalp in the above scenarios because current approaches are not adapted to help the user reach areas on their scalp and apply a treatment without disturbing the user's natural or artificial hairstyle.

The information included in this Background section of the specification, including any references cited herein and any description or discussion thereof, is included for technical reference purposes only and is not to be regarded subject matter by which the scope of the invention as defined in the claims is to be bound.

SUMMARY

In accordance with various embodiments, a therapeutic scalp care tool for treating skin ailments may include a body having a first end and second end and an exterior wall suitable to be held in a user's hand and defining an interior cavity. The system may further include a treatment operable to provide a therapeutic benefit to a person's scalp. The treatment may be located within the cavity. A flow control may be operable to contain the treatment within the interior cavity and release the treatment through a passage in response to actuation of the flow control. The flow control may be located to receive the treatment from the cavity and control the passage of the treatment through the passage. The system may further have an applicator on the first end of the body in fluid communication with the flow control and having a tip defining an outlet within a distal surface thereof in fluid communication with the passage, wherein the distal surface of the tip is configured to contact the person's scalp, is sized to fit between a part or rows of hair, and is suitably large to provide itch relief without cutting the person's scalp. The applicator end may include a passage that is in fluid communication with the flow control. In accordance with various embodiments, the treatment may include at least one of a medication, lotion, oil, or cleanser.

The second end may include a second tip forming a point sized to fit between the part or rows of hair and suitably large to provide itch relief without cutting the scalp. The second end may have a filling aperture open to the cavity operable to fill the cavity with the treatment. The filling aperture may receive a removable cap operable to retain the treatment in the cavity on the second end. The removable cap may include a second tip forming a point sized to fit between the part or rows of hair and suitably large to provide itch relief without cutting the scalp. The second tip may help push oils, moisturizers, and medicaments reach under artificial hair attachments, for example, to provide treatments for dandruff and psoriasis. This tool can be an applicator for treatment. The flow control may be located proximal to the first end. The applicator end may include a passage that extends from the cavity to the tip. The flow control may include a ball located in a socket within the applicator. The ball may be operable to rotate freely within the socket allowing treatment to escape around the ball as it rotates. The ball may provide a rounded profile to the tip.

In accordance with various embodiments, the flow control may include a valve located between the applicator end and the body that is operable to restrict the flow of treatment from the cavity to the outlet in the tip. The valve may include a rotatable collar that defines an opening and is movable from a first position to a second position. In the first position, the opening may be aligned with the passage in the applicator end allowing flow of treatment from the cavity to the outlet and in the second position, the opening may be misaligned with the passage in the applicator end thereby limiting the flow of treatment from the cavity to the outlet.

The applicator defines the passage that extends from the cavity to the tip and the opening through the rotatable collar and an entry to the passage through the applicator end may be offset from a center axis about which the rotatable collar rotates. Alternatively or additionally, the applicator end may be threaded onto the body and the flow control, which may include an obstruction that is positioned to engage the passage in response to the applicator end being threaded towards the body. Alternatively or additionally, the flow control may include a ball and spring located in a cavity within the passage in the applicator. The ball may be forced against the outlet by the spring such that pressure on the ball opens the outlet, allowing treatment to flow out of the outlet.

In accordance with various embodiments, the system may further have a second flow control device which modifies the flow out of the outlet. The first and second flow control devices may include any combination of the devices discussed above. For example, the second flow control may include a ball located in a socket within the applicator, wherein the ball is operable to rotate freely within the socket allowing treatment to escape around the ball as it rotates. The first flow control may include the collar discussed above.

In accordance with various embodiments, the system may further have a removable reservoir formed within the interior cavity of the body to hold the treatment and in fluid communication with the outlet and the treatment being located within the removable reservoir.

In accordance with various embodiments, a therapeutic method for treating a scalp ailment may comprise a method including obtaining a treatment tool. The treatment tool may include a body having a first end and a second end and an exterior wall suitable to be held in a user's hand and defining an interior cavity. The treatment tool may also include a treatment within the interior cavity operable to provide a therapeutic benefit to the person's scalp. The treatment device may also include a flow control operable to contain the treatment within the interior cavity and release the treatment from the interior cavity through a passage in response to actuation of the flow control. The treatment device may also include an applicator on the first end of the body in fluid communication with the flow control and having a single tip defining an outlet within a distal surface thereof in fluid communication with the passage, wherein the distal surface of the tip is configured to contact the person's scalp, forms a point sized to fit between a part or rows of hair, and is suitably large to provide itch relief without cutting the person's scalp. The body may be in communication with the outlet on the first end. The tip may be applied to the scalp. The treatment may be released to the scalp through the outlet. The ailment may be relieved by massaging an area occupied by the ailment with the tip of the treatment tool and the treatment.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 4A illustrates a schematic side elevation view of an enlarged fragment in cross-section of a skin treatment tool taken along line B-B as shown in FIG. 3A in accordance with one embodiment.

FIG. 4B illustrates an enlarged, schematic, top plan view in cross-section of the skin treatment tool taken along line C-C shown in FIG. 4A in accordance with one embodiment.

DETAILED DESCRIPTION

Multiple embodiments of skin treatment tools that include both mechanical treatment and therapeutic treatment characteristics are disclosed herein. The disclosed tool can provide relief to the skin and, more particularly, the scalp by applying a therapeutic treatment such as a moisturizer while also applying physical relief in the form of scratching. The therapeutic treatment may be contained within the tool and delivered via an outlet which also doubles as a scratching tool that is able to reach the scalp directly by fitting within the hair style such as braids, weaves, extensions or the like.

Figure 1:
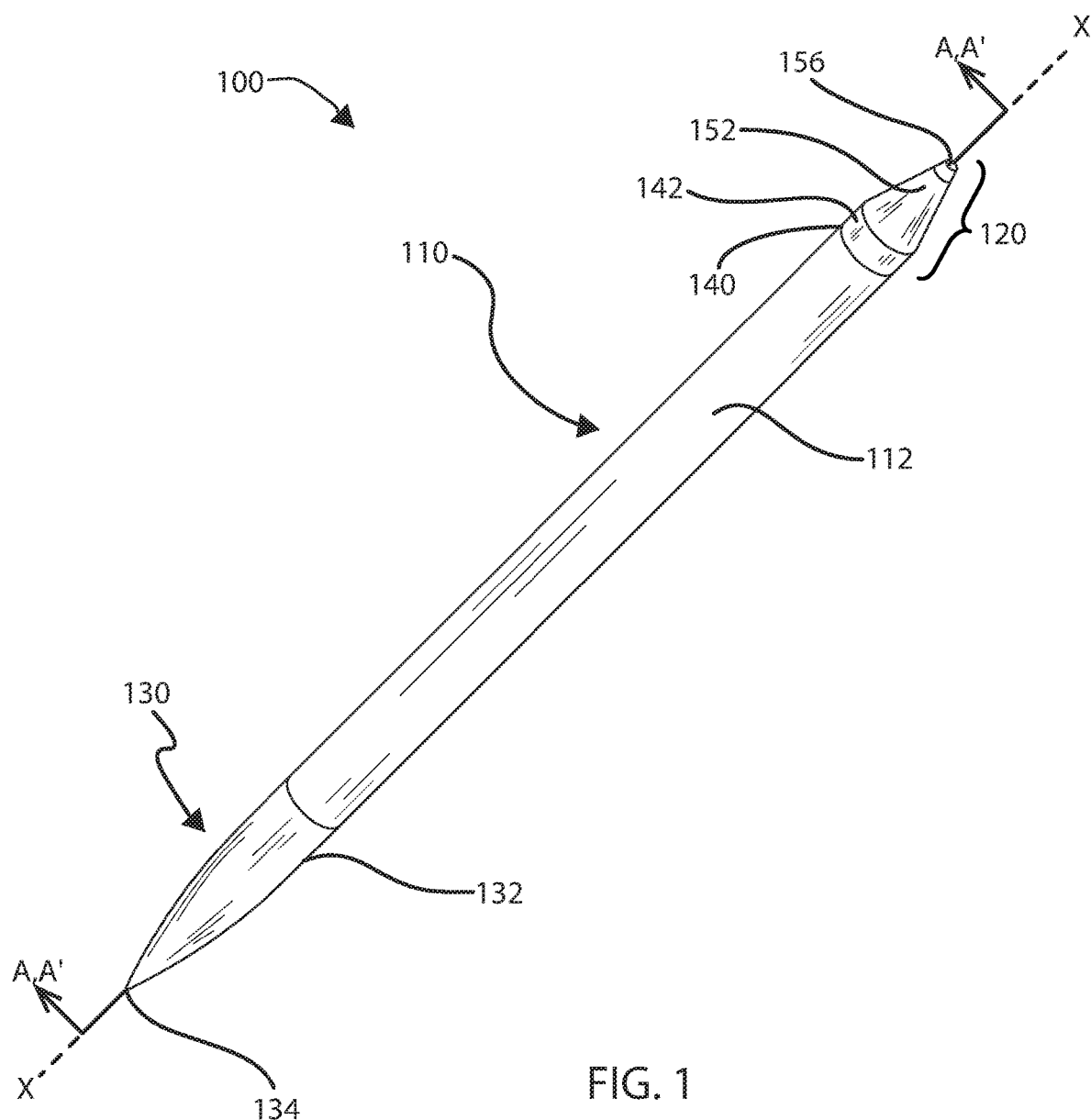
FIG. 1 illustrates a schematic isometric view of a skin treatment tool in accordance with various embodiments.

In accordance with various embodiments, as shown in FIG. 1, which illustrates a schematic isometric view of a skin treatment tool 100, the skin treatment tool 100 may include a body 110, an applicator 120 at an applicator end 119, a cap 130 at a filling end 117, and a therapeutic treatment 180. The body 110 may be defined by an exterior wall 112. The body 110 may be cylindrical with a central axis X. The central axis X may define the center of the body 110, the cap 130, and the applicator 120. This cylindrical shape may extend to the filling aperture 118 and the aperture 113 causing them to be cylindrical as well. In other embodiments, the exterior wall 112 may be symmetric, non-symmetric, or any other shape. The exterior wall 112 may be shaped such that it is operable to be held in a user's hand. The body 110 may be sized such that the skin treatment tool 100 may be carried in a handbag or purse.

Figure 3A:
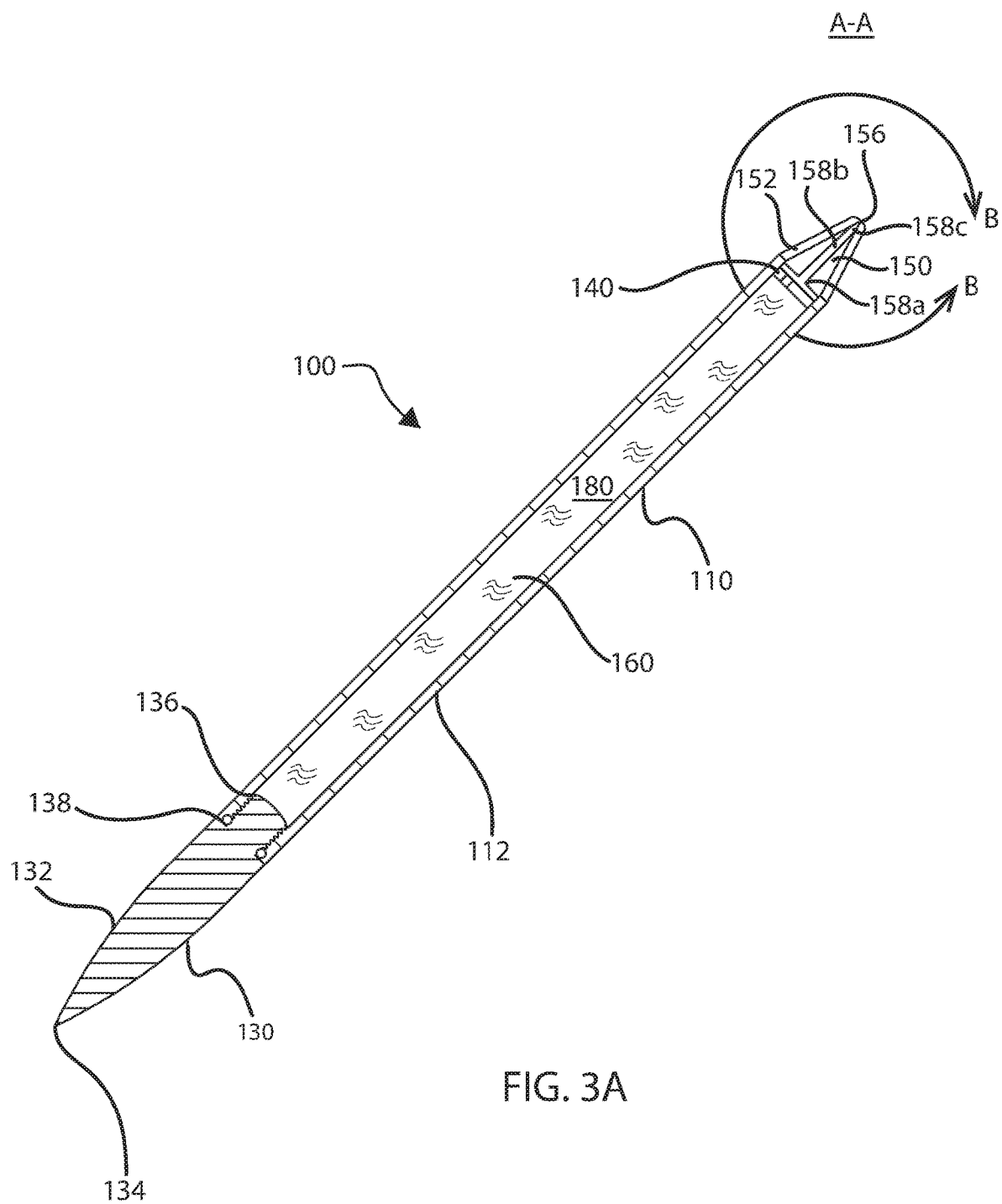
FIG. 3A illustrates a schematic side elevation view in cross-section of a skin treatment tool taken along line A-A shown in FIG. 1 in accordance with one embodiment.

As shown in FIG. 3A, the exterior wall 112 may define an interior cavity 160. The body 110 may contain the therapeutic treatment 180 within the interior cavity 160. The therapeutic treatment 180 may be released through the applicator 120. The skin treatment tool 100 may additionally include one or more types of manually operated flow controls 140. The manually operated flow control 140 may limit the release of the therapeutic treatment 180 through the applicator 120. In some embodiments, an automatic flow control 150 may be employed in combination with the manually operated flow control 140. The exterior wall 112 may be shaped such that the cavity 160 defined thereby is suitably sized to contain at least a single therapeutic amount of the treatment. The cavity 160 may be sized to contain more than a single therapeutic amount of the therapeutic treatment 180 such that multiple applications of the therapeutic treatment 180 may be applied to a skin surface.

The applicator end 119 may be on an opposite end of the body 110 from the filling end 117. The applicator 120 may mate with at least one of the manually operated flow control 140 or the applicator end 119. The applicator end 119 may include an aperture 113 to receive the applicator 120 and which allows the treatment to flow to the applicator 120. Alternatively, the aperture 113 may allow for the insertion of a separate reservoir 161 within the interior cavity to extend therethrough and engage and feed the therapeutic treatment 180 to the applicator 120. The filling end 117 may mate with the cap 130. On the other end of body 110, the filling end 117 may include a filling aperture 118. The filling aperture 118 may be operable to allow the therapeutic treatment 180 through to fill the cavity 160. Alternatively, the filling aperture 118 may allow for the insertion of a separate reservoir 161 within the interior cavity to extend therethrough.

Figure 3B:
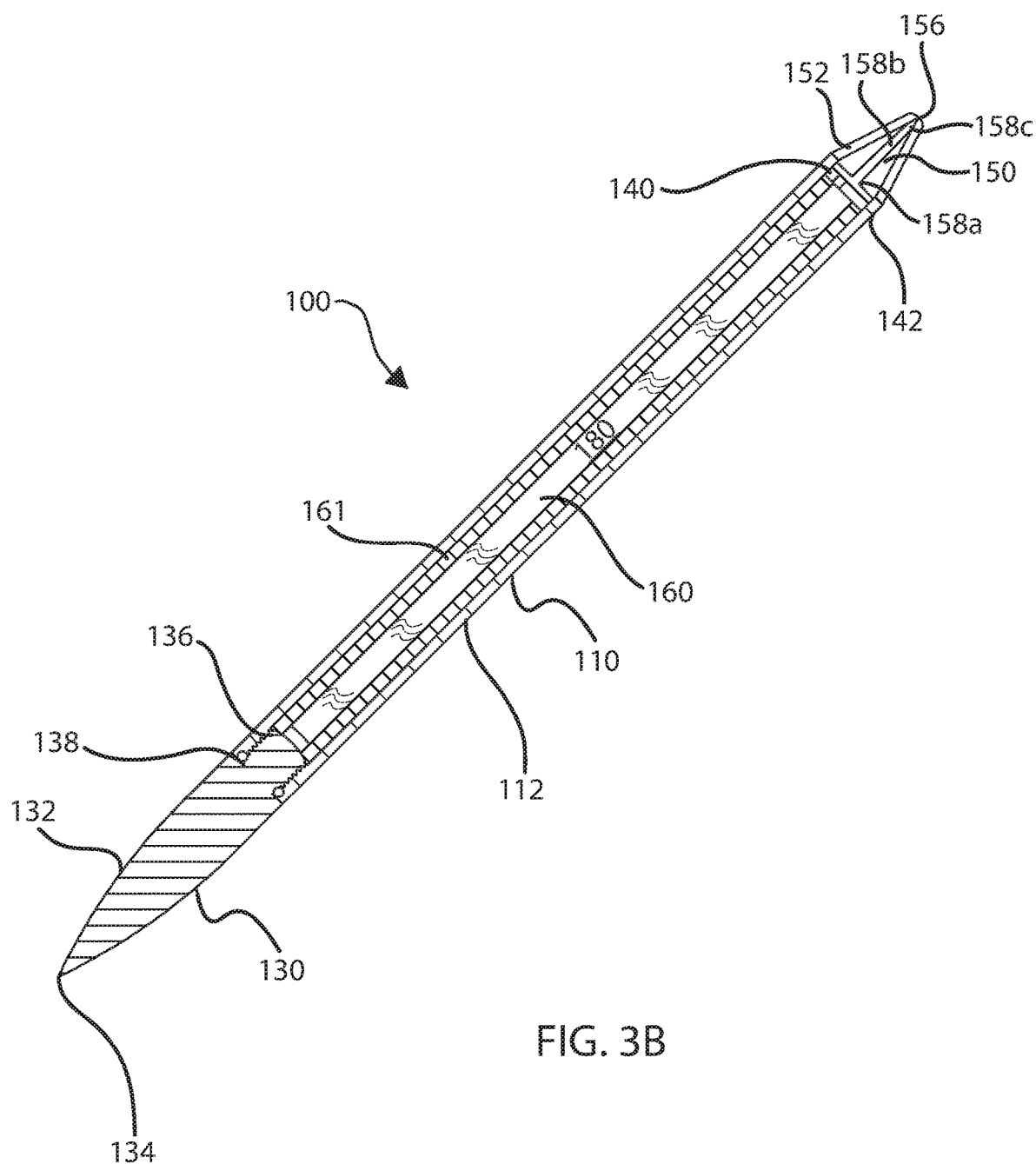
FIG. 3B illustrates a schematic side elevation view in cross-section view of a skin treatment tool taken along line A-A shown in FIG. 1 in accordance with another embodiment (denoted as A'-A' to distinguish over the embodiment shown in FIG. 3A).

As noted, in various embodiments, as shown in FIG. 3B, the cavity 160 may contain a reservoir 161. The reservoir 161 may be a secondary container for the therapeutic treatment 180 that fits within the cavity 160. The reservoir 161 may be a reloadable and/or removable cartridge containing the therapeutic treatment 180. In some implementations, the reservoir 161 may be disposable. The reservoir 161 may be a barrier operable to separate the treatment from the exterior wall 112. The therapeutic treatment 180 may be contained within the reservoir 161 and may be fluidly connected with one or more of the manually operated flow control 140, the applicator 120, and the automatic flow control 150.

The applicator 120 may be defined by an exterior surface 152. The exterior surface 152 may taper to a therapeutic tip 156. The taper of the exterior surface 152 may decrease the diameter of the applicator 120 until the therapeutic tip 156 may be sized to fit between the follicles, part or rows of hair. Additionally or alternatively, the therapeutic tip 156 may be suitably large to provide itch relief without cutting the skin. The therapeutic tip 156 may be solid with a rounded end operable to massage the skin without breaking it. The rounded end may be sufficiently small to provide itch relief. The end 120 and particularly the therapeutic tip 156 may provide mechanical relief along with an outlet to dispense the therapeutic treatment 180 to the affected skin.

Figure 2:
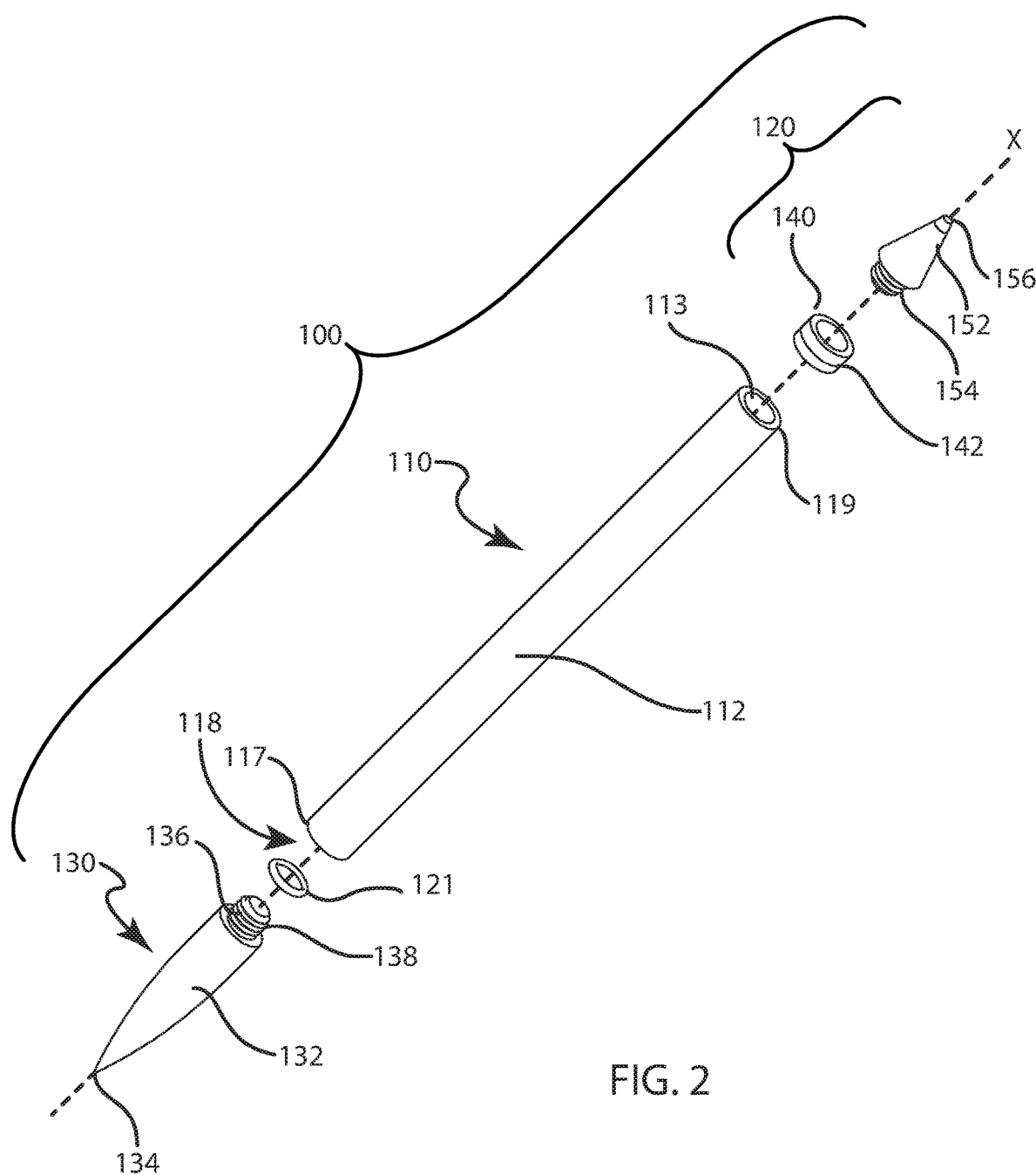
FIG. 2 illustrates a schematic exploded isometric view of the skin treatment tool in accordance with various embodiments.

As illustrated in FIG. 2, the applicator 120 may include an engagement end 154 that is operable to engage the aperture 113 at the filling end 117. The engagement may be any fit operable to prevent or limit the therapeutic treatment 180 from flowing out of the aperture 113. In one example, this engagement may be a threadable engagement. In other embodiments, the engagement may be a press fit or a snap fit. Adhesive or welding, e.g., and ultrasonic weld, may be used to create a fluid-tight connection. In other embodiments, a sealing structure, e.g., an O-ring 121, may be used between the engagement end 154 and the aperture 113 of the filling end 117 or the flow control 140 to provide a fluid-tight seal. The applicator 120 may include an opening 158a proximal to the engagement end 154. The opening 158a may open into a passage 158b. The passage 158b may extend longitudinally though the applicator 120 exiting from the applicator 120 at an outlet 158c. The outlet 158c may be proximal to the therapeutic tip 156. In various embodiments, the opening, passage, and outlet 158a/b/c may be in direct fluid communication with the therapeutic treatment 180 housed within the cavity 160 or the reservoir 161. In other embodiments, the opening, passage, and outlet 158a/b/c may be in indirect fluid communication with the therapeutic treatment 180 housed within the cavity 160 or the reservoir 161, being separated by one or more flow controls.

In accordance with various embodiments, a skin treatment tool may include a therapeutic skin treatment 180. The therapeutic treatment 180 may include any substance that provides a therapeutic benefit topically applied to skin or, more particularly, the scalp. The therapeutic treatment 180 may include cleansers, oils, lotions, toners, medication or other therapeutic products. For example, the treatment may be a skin moisturizer such as coconut oil or a medication such as witch hazel. Utilizing the treatment tool, the therapeutic treatment may be applied directly to the scalp while also applying mechanical treatment (e.g., itch relief). In another embodiment, the therapeutic treatment 180 may be cosmetic in nature. For example, the treatment may be a type of makeup such as foundation. In this regard, the treatment tool may be utilized at the hair line to blend the foundation on the face with the difficult to reach skin obstructed by hair at the hair line. In accordance with various embodiments, the treatment may also be any other topical skin treatment products which may be beneficial to a user on any area of the skin but particularly as applied to the scalp.

As shown in FIG. 3b, the cap 130 may be defined by an exterior wall 132. The cap 130 may be a solid element as shown or hollow and tubularly formed. The cap 130 may have an engagement end 136 operable to engage the filling end 117. In one example, the engagement end 136 may engage with the filling aperture 118. The engagement may be any fit operable to contain the therapeutic treatment 180 within the cavity 160. In this way the cap 130 may be operable as a cap that is removable for filling or refilling the cavity 160 with the therapeutic treatment 180. A sealing structure, for example, an O-ring 121, may be positioned between the engagement end and an inside surface of the exterior wall 112 defining the filling aperture 118 In one example, the engagement between the engagement end 136 and the filling aperture 118 may be a threaded engagement. In other embodiments, the engagement may be a press fit or a snap fit. In the example of FIG. 3B, the engagement end 136 may be a protrusion from the exterior wall 132 that is sized and shaped to engage the filling aperture 118. The engagement end 136 may be smaller in diameter than the largest portion of the exterior wall 132. The engagement end 136 may have threads which thread into opposing threads within the filling aperture 118. The cap 130 may also include an engagement surface 138 which mates with the filling end 117 of the body 110.

In accordance with various embodiments, the cap 130 may be operable as a second therapeutic mechanical device. For example, the exterior wall 132 may taper to a therapeutic tip 134. The therapeutic tip 134 may be sized to fit between the follicles, part or rows of hair. Additionally or alternatively, the therapeutic tip 134 may be suitably large to provide itch relief without cutting the skin. The therapeutic tip 134 may be solid with a rounded end operable to massage the skin without breaking it. The rounded end may be sufficiently small to provide itch relief. The cap 130 and particularly the therapeutic tip 134 may provide mechanical relief without an outlet to dispense treatment to the affected skin. However, in other embodiments, the cap 130 may be a comb, a brush, or some other form of hair care device.

The skin treatment tool 100 may include one or more flow control mechanisms operable to contain, restrict, and/or selectably allow the therapeutic treatment 180 to flow from the cavity 160 or reservoir 161. Flow controls may be manually activated or they may be automatically actuated. A manually operated flow control 140 may be actuated by a user by selecting an active or inactive state to control of the flow of the therapeutic treatment 180. In one example, the manually operated flow control 140 may be positioned between the body 110 and the applicator 120. Before use, a user may manipulate the control (e.g., an exterior surface 142) causing the treatment tool 100 to enter an active state and allowing the therapeutic treatment 180 to flow past the manually operated flow control 140. In various embodiments, which may be included together with or separately from the manually operated flow control 140, an automatic flow control 150 may be included in the treatment tool 100' as shown in FIG. 3B. An automatic flow control 150 may be one in which usage of the treatment tool 100 allows the therapeutic treatment 180 to flow from the tool 100 without manual activation (e.g., opening of a valve) by a user. Embodiments of treatment tools may have only an automatic flow control 150, only a manually operated flow control 140, a combination of both, a plurality of one, a plurality of the other, or a plurality of both.

In accordance with various embodiments, as illustrated in FIGS. 3A and 3B, the automatic flow control 150 may comprise the opening, passage, and outlet 158a,b,c. In this embodiment, the opening, passage, and outlet 158a,b,c may be smaller in diameter than the cavity 160 or the reservoir 161 thereby restricting and slowing the flow of treatment out of the cavity 160. Thus, the flow may be controlled by merely throttling the flow to a smaller passage.

In another exemplary embodiment as illustrated in FIGS. 4A and 4B, an applicator 420 may include an opening 458a which opens proximal to a manually operated flow control 440 above the cavity 160. The opening 458a may be an entrance to a passage 458b that extends through the applicator 420 (similar to the applicator 120 discussed above). The passage 458b may exit at an outlet 458c. The outlet 458c may be blocked by an obstruction 457. In one example, the outlet 458c may exit into a receptacle 459. The receptacle 459 may be a socket that the obstruction 457 may snap into such that obstruction 457 is not easily removed therefrom. The receptacle 459 may be located proximal to a therapeutic tip 456 (similar to the therapeutic tip 156 discussed above). The receptacle 459 may retain the obstruction 457. In one example, the obstruction 457 may be a ball located in the receptacle 459. The engagement between the obstruction 457 and the receptacle 459 may be such that the obstruction 457 is operable to rotate. As the obstruction 457 rotates, it may allow the therapeutic treatment 180 to pass out of outlet 458c, into the receptacle 459, and out of the therapeutic tip 456. Contact of the obstruction 457 against skin may cause the obstruction 457 to rotate, thereby releasing the treatment. The obstruction 457 may be a part of the therapeutic tip 456 and have the same profile, namely that the combination of the obstruction 457 and the therapeutic tip 456 may be sized to fit between the follicles, part, rows, weave, or extensions of hair and contact the scalp directly. Additionally or alternatively, the therapeutic tip 456 and the obstruction 457 combination may be suitably large to provide itch relief without puncturing or cutting the skin.

In accordance with various embodiments, as shown in FIGS. 4A-4B, a manually operated flow control 440 may include a rotatable collar 442. The collar 442 may define a passage 448 therethrough. The rotatable collar 442 may be movable from a closed first position 1 to an open second position 2. In the first position 1, the passage 448 and the opening 458a within the passage 458b may be in different positions (i.e., unaligned or substantially unaligned) such that flow of the therapeutic treatment 180 is limited or prevented from exiting the cavity 160. In the second position 2, the passage 448 in the collar 442 may be aligned with the opening 458a. The second position 2 may thus allow the flow of the therapeutic treatment 180 from the cavity 160 to the outlet 458c.

The rotatable collar 442 may be rotatable by having slideable engagements between one or both of the applicator 420 and the body 110. The slideable engagement may include a tab or flange 443. The flange 143 may extend away from the rotatable collar 442 toward the exterior surface 452. The flange 443 may be a continuous annular protrusion extending from the rotatable collar 442. Alternatively, the flange 443 may be a plurality of discrete tabs extending from the collar 442. The flange 443 may engage a corresponding lip 453 on the applicator 420. The lip 453 may likewise be annular. The engagement of the flange 443 and lip 453 together may allow for rotational movement between the collar 442 and the applicator 420. This movement is shown in FIG. 4B, from 1 to 2, which illustrates how passage 448 may rotate around to align with the opening 458a shown as a hidden line. This relative rotational movement between the collar 442 and the manually operated flow control 440 may allow the alignment and misalignment of the passage 448 and the passage 458b. The body 110 may likewise have a lip or tabs 111 operable to engage the flange 443 on the collar 442, allowing for relative rotational movement between the body 110 and the manually operated flow control 440 as well. However, in another embodiment, this may be a fixed relationship such that there is no relative rotational movement between the body 110 and the manually operated flow control 440.

FIGS. 4A and 4B show the treatment tool 100 with examples of both the manually operated flow control 440 and an automatic flow control in the form of the occlusion 457 in the applicator 420 but, as indicated above, this is merely an example as the treatment tool 100 may include only one or the other.

Figure 5A:
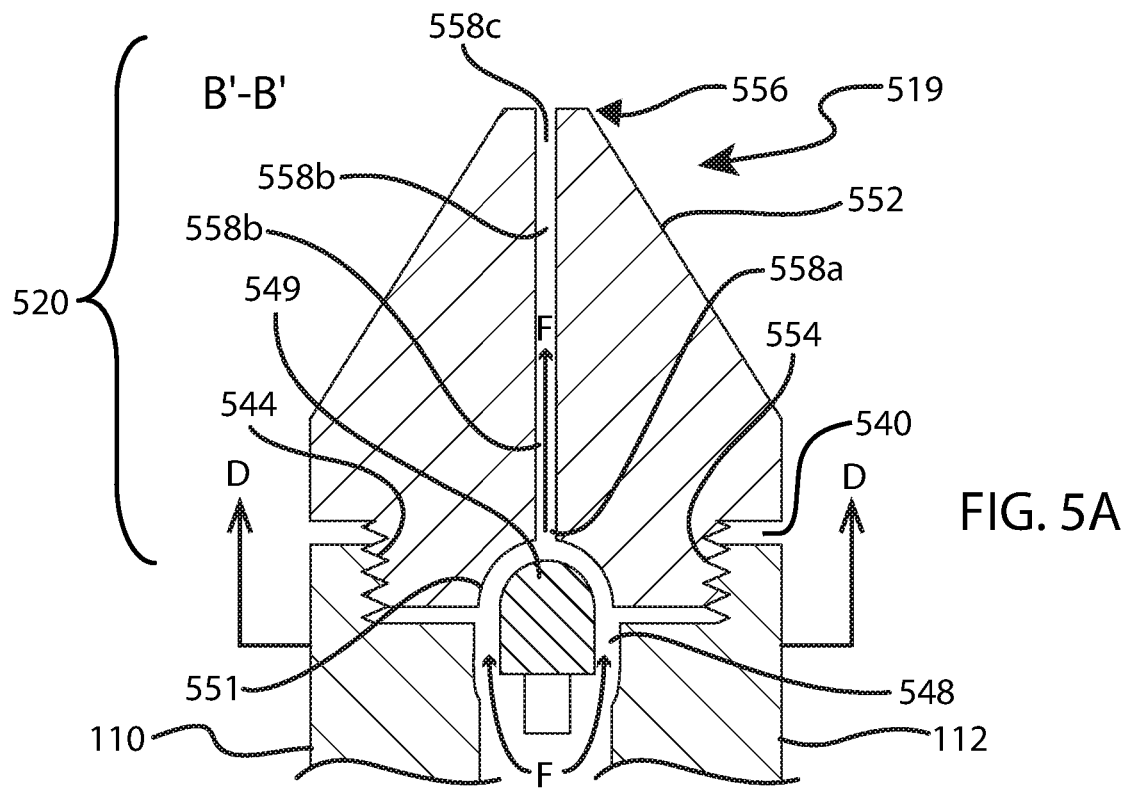
FIG. 5A illustrates a schematic side elevation view of an enlarged fragment in cross-section of a skin treatment tool taken along line B-B shown in FIG. 3A in accordance with another embodiment (denoted as B'-B' to distinguish over the embodiment shown in FIG. 4A).
Figure 5B:
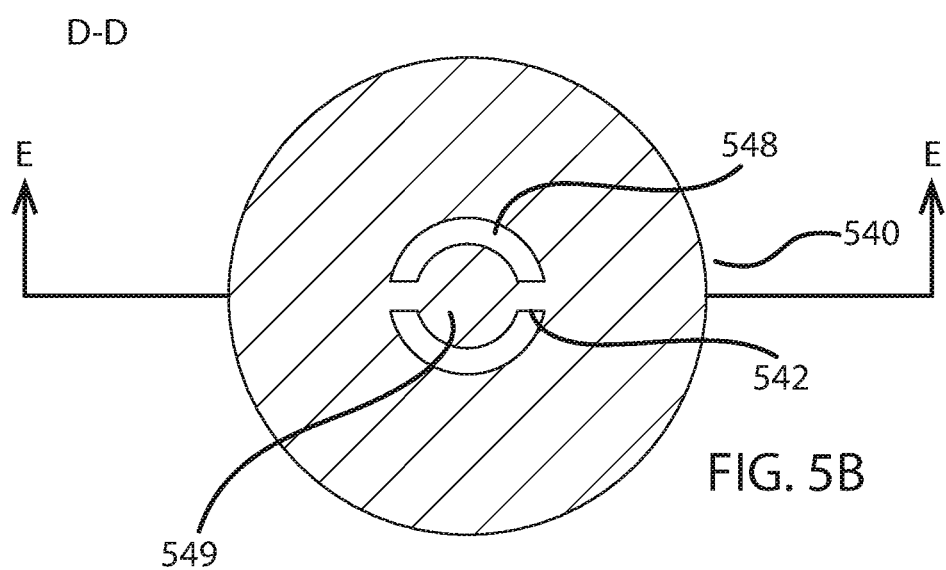
FIG. 5B illustrates an enlarged, schematic, top plan view in cross-section of the skin treatment tool taken along line D-D shown in FIG. 5A in accordance with one embodiment.
Figure 5C:
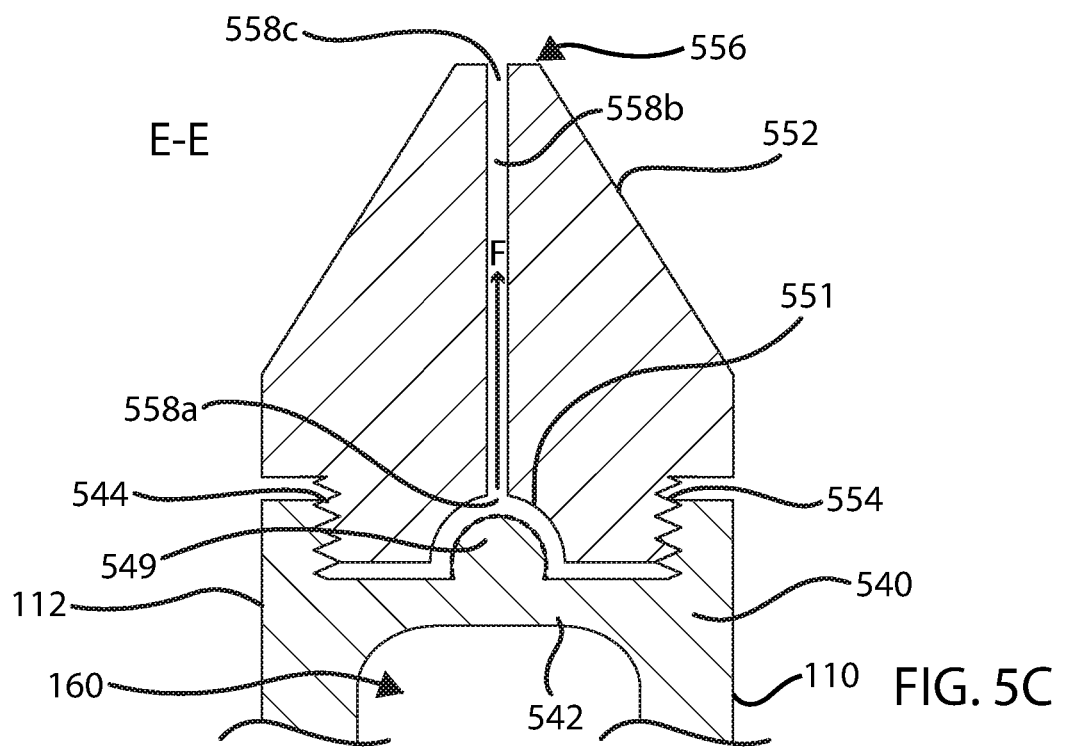
FIG. 5C illustrates an enlarged, schematic, side elevation view in cross-section of the skin treatment tool taken along line E-E shown in FIG. 5B in accordance with one embodiment.

In another exemplary implementation as shown in FIGS. 5A-C, the treatment tool 100 may include a flow control 550. FIG. 5A illustrates an example of an enlarged view of the applicator end 519 similar to the area indicated by line B-B in FIG. 3A. FIG. 5A is shown as B'-B' to distinguish this embodiment over the embodiment represented in FIG. 4A which is a different but applicable example of the B-B area. The flow control 550 may be removably attached to the body 110, fixed to body 110 or integral with the body 110. A manually operated flow control 540 may include a threaded engagement along an annular surface 544. The applicator 520 may include a threaded engagement along an annular surface 554 which may be between an exterior surface 552 and the end of the body 110. The annular threaded surface 554 and the annular threaded surface 544 may engage and thread into one another. The threaded engagement may contract the applicator end 520 towards the flow control 550 in response to threading the applicator end 520 into body 110.

The manually operated flow control 540 may further include an obstruction 549. The manually operated flow control 540 may further define a passage 548. The applicator 520 may include a mating surface 551 located proximal to the opening 558*a*. The mating surface 551 may receive the obstruction 549 in response to threading the applicator end 520 onto the body 110. The mating surface 551 may be any size or shape suitable to receive the obstruction 549. In one example, the mating surface 551 may be substantially the same size and shape as the obstruction 549. In another example, the mating surface 551 may merely be a transitional surface around the opening 558*a*. The obstruction 549 which is a part of the manually operated flow control 540 may be any suitable shape and size to block the flow into the opening 558*a* in response to being forced against the mating surface 551. In one example, the obstruction 549 may have a substantially spherical end which engages with the mating surface 551. The mating surface 551 may have a correspondingly substantially spherical cavity configured to receive the obstruction 549. The obstruction 549 and the mating surface 551 may nest together such that the obstruction 549 blocks and seals the passage 558*b*, preventing the therapeutic treatment 180 from flowing through the passage 558*b*.

The obstruction 549 may be attached to the external wall 112 by a bridge 542 as shown in FIG. 5C. The bridge 542 may extend from the obstruction 549 to the exterior wall 112 such that the obstruction 549 is held in place and may engage the mating surface 551 with a force in the flow direction F as shown in FIG. 5A. The force may be suitable to close the passage 558*b* and limit or prevent the therapeutic treatment 180 from flowing through the passage 558*b*. The bridge 542 may have passages 548 that bypass the obstruction 549 as shown in FIG. 5B such that the therapeutic treatment 180 may flow around the obstruction 549 in response to the applicator end 520 and the manually operated flow control 540 not being engaged. As an example, the passage 548 may be formed around two sides of the obstruction 549 as shown in FIGS. 5A and 5B. The therapeutic treatment 180 may flow from the cavity 160 through the passage 548, into the opening 558*a*, through the passage 558*b*, and out of the outlet 558*c* proximal to the therapeutic tip 556. This path is shown along arrows F (shown in FIG. 5A). This flow may be possible when the applicator end 520 and the body 110 are not compressed toward each other by threading into one another. A user may thread the applicator end 520 and the body 110 into one another, thereby closing the opening 558*a* by compressing the applicator end 520 and the body 110 towards each other utilizing the threadable engagement. This results in the treatment being prevented or limited in its escape from the treatment tool 100.

In some exemplary embodiments, the treatment tool 100 may include various additional features such as a brush, a comb, a hair pick or the like. As discussed above, a second end of the treatment tool 100 may be a non-treating scratch end. This non treating end may be an integral of the part of the body 110, or part of an attachable portion such as cap 130 which may be operable as a cap. In this way the skin treatment tool 100 may be able to apply a mechanical and therapeutic treatment from one end and only a mechanical treatment from a second end.

Figure 6:
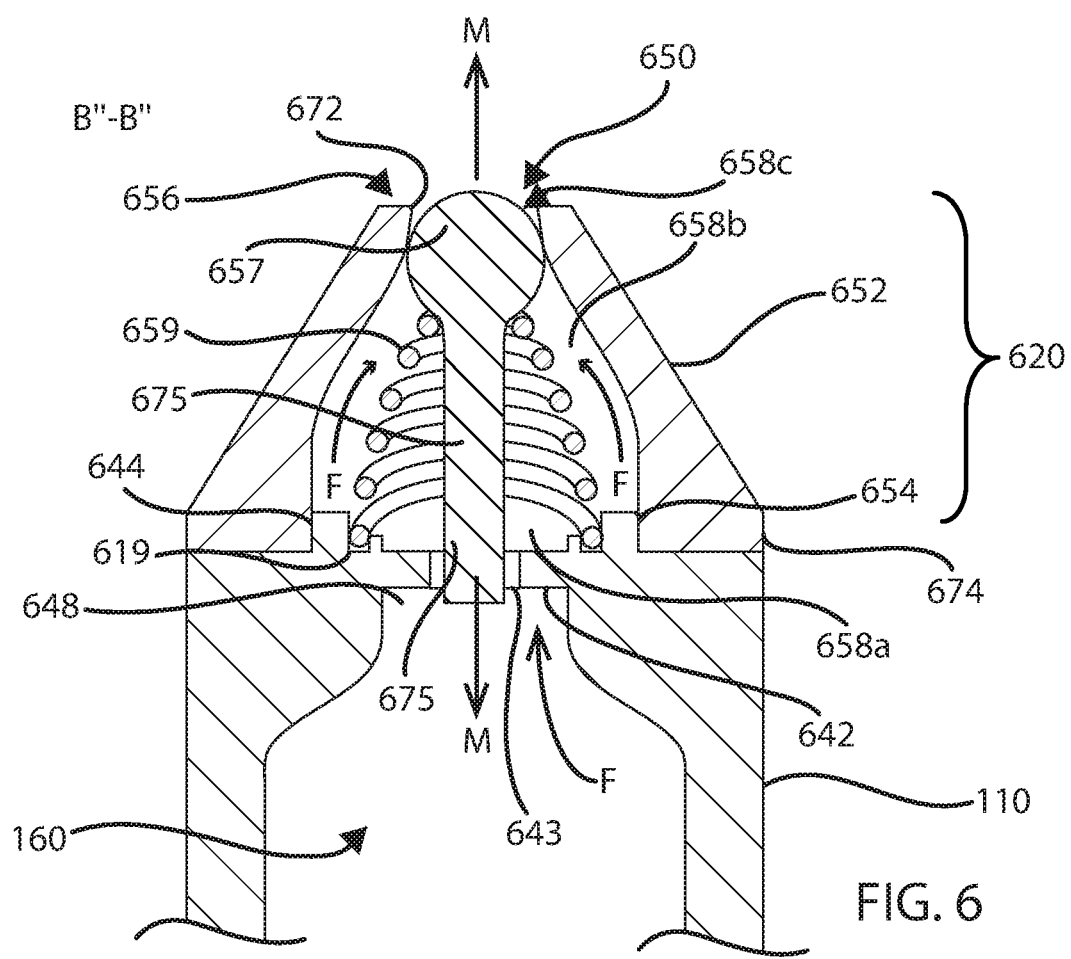
FIG. 6 illustrates an enlarged, schematic, side elevation view in cross-section of a skin treatment tool taken along lines B-B as shown in FIG. 3A in accordance with one embodiment (denoted as B"-B" to distinguish over the embodiment shown in FIG. 4A).

In another exemplary embodiment, the flow of the therapeutic treatment 180 may be manipulated by an automatic flow control 650 illustrated in FIG. 6. The automatic flow control 650 may be located within an applicator 620. The applicator 620 may be similar to the applicator 120 and the applicator 420 discussed above, being defined by an exterior wall 652 (similar to exterior surface 152 and exterior surface 452) with a passage 658*b* extending therethrough. The passage 658*b* may exit proximal to the applicator tip 656 at an outlet 658*c*. The outlet 658*c* may include an interior wall 672 proximal to the opening at the applicator tip 656. The automatic flow control 650 may include an obstruction 657 which is movably located within the outlet 658*c*. In a first position, the obstruction 657 may contact the interior wall 672 thereby closing the passage 658*b* at the outlet 658*c*. In a second position, the obstruction 657 may be moved out of contact with the interior wall 672, thereby opening a space around the obstruction to connect the passage 658*b* and the outlet 658*c* allowing fluid to pass therethrough. The movement between the first and second position may follow the arrow M shown in FIG. 6.

The obstruction 657 may be biased against the interior wall 672. In one example, a spring 659 may be position between a support surface 619 and the obstruction 657. This position may allow the spring 659 to force the obstruction 657 away from the support surface 619 and toward the interior wall 672. The applicator 620 may be mated against the support surface 619. The applicator 620 may additionally or alternatively be concentric with an annular wall 644 extending from the support surface 619. The motion may be restrained by a stud 675 extending downward from the obstruction 657. The stud 675 may pass through an annular ring 643 supported by a bridge 642 (similar to the bridge 542 in FIGS. 5A-5C). The stud 675 may slide through the annular ring 643, which helps maintain the axial orientation of the stud 675 and thus the obstruction 657.

An interior surface 654 on an end 674 proximal to the support surface 619 may engage the annular wall 644, thereby attaching the applicator 620 to the body 110. In some embodiments, the interior surface 654 and the annular wall 644 may be sealed together, for example, by adhesive or by ultrasonic welding, for example if the body and the applicator wall 652 are both made of plastic. In this structure, the therapeutic treatment 180 may flow from the cavity 160 into a passage 648 and then into the opening 658*a*, through the passage 658*b*, and out of outlet 658*c* which is proximal to the therapeutic tip 656. The treatment may then be obstructed by the obstruction 657 in a first position and unobstructed by the obstruction 657 in the second position.

In accordance with various embodiments, the treatment tool 100 may be manufactured as a single integral device, multiple connected devices, or a combination thereof. Any one or more of the elements of the treatment tool 100 may be machined, cast, molded, formed, or manufactured from any known process or developed process. Any one or more of the elements of the treatment tool 100 may be formed from a metal, polymer, wood, glass, composite material or any known material or developed material.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

As used herein, the terms "a", "an", "one or more", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

All relative and directional references (including: upper, lower, upward, downward, left, right, leftward, rightward, top, bottom, side, above, below, front, middle, back, vertical, horizontal, height, depth, width, and so forth) are given by way of example to aid the reader's understanding of the particular embodiments described herein. They should not be read to be requirements or limitations, particularly as to the position, orientation, or use of the invention unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

Unless otherwise indicated, all numbers expressing properties, sizes, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, numbers are not approximations unless the word "about" is recited.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A therapeutic scalp care tool comprising
a body having a first end and a second end and an exterior wall suitable to be held in a user's hand and defining an interior cavity;
a treatment operable to provide a therapeutic benefit to a person's scalp, the treatment located within the interior cavity;
a flow control operable to contain the treatment within the interior cavity and release the treatment from within the interior cavity through a passage in response to actuation of the flow control, the flow control being located to receive the treatment from the interior cavity and control a flow of the treatment through the passage;
an applicator on the first end of the body in fluid communication with the flow control and having a tip defining an outlet within a distal surface of the tip in fluid communication with the passage, wherein the distal surface of the tip is configured to contact the person's scalp, is sized to fit between a part or rows of hair, and includes a rounded end to provide itch relief without cutting the person's scalp; and
a cap on the second end of the body, wherein
the cap is configured to removably attach to the second end of the body and close a filling aperture in the second end of the body open to the interior cavity,
the filling aperture is operable to fill the interior cavity,
the cap defines a second tip that does not include a fluid outlet, and
the cap is formed as a solid body or a sealed hollow body including an engagement end configured to seal the filling aperture and an exterior surface forming the exterior of the therapeutic scalp care tool.

2. The therapeutic scalp care tool of claim 1, wherein the treatment includes at least one of a medication, lotion, oil, or cleanser.

3. The therapeutic scalp care tool of claim 1, wherein the second tip is sized to fit between the part or rows of hair and to provide itch relief without cutting the person's scalp.

4. The therapeutic scalp care tool of claim 1, wherein the filling aperture receives the cap which is operable to retain the treatment in the interior cavity on the second end.

5. The therapeutic scalp care tool of claim 4, wherein the second tip forms a point sized to fit between the part or rows of hair and to provide itch relief without cutting the person's scalp.

6. The therapeutic scalp care tool of claim 1, wherein the flow control is located proximal to the first end.

7. The therapeutic scalp care tool of claim 1, wherein the applicator defines the passage that extends from the interior cavity to the tip and the passage forms the outlet as the passage extends through the tip.

8. The therapeutic scalp care tool of claim 1, wherein the flow control includes a ball located in a socket within the applicator and the ball is operable to rotate freely within the socket allowing the treatment to escape around the ball as the ball rotates.

9. The therapeutic scalp care tool of claim 8, wherein the ball provides a rounded profile to the tip.

10. The therapeutic scalp care tool of claim 1, wherein the flow control is a manually actuated valve located between the applicator and the body that is operable to restrict the flow of the treatment from the interior cavity to the outlet in the tip.

11. The therapeutic scalp care tool of claim 10, wherein
the valve includes a rotatable collar defining an opening and the rotatable collar is movable from a first position to at least a second position;
the first position aligns the opening with the passage allowing the flow of the treatment from the interior cavity to the outlet; and
the second position dislocates the opening from the passage thereby restricting the flow of the treatment from the interior cavity to the outlet in the tip.

12. The therapeutic scalp care tool of claim 11, wherein
the applicator defines the passage that extends from the interior cavity to the tip; and the opening through the rotatable collar and an entry to the passage through the applicator are offset from a center axis about which the rotatable collar rotates.

13. The therapeutic scalp care tool of claim 10, wherein
the applicator is threaded onto the body; and
the flow control further comprises an obstruction positioned to engage and restrict the passage in response to the applicator being threaded toward the body.

14. The therapeutic scalp care tool of claim 10 further comprising a ball located in a socket within the applicator, wherein the ball is operable to rotate freely within the socket allowing the treatment to escape around the ball as the ball rotates.

15. The therapeutic scalp care tool of claim 1, wherein
the flow control includes an obstruction and a spring located in the passage within the applicator;
the obstruction is biased against sides of the outlet in the tip by the spring such that pressure on the obstruction resists the spring bias to open the outlet and allow the treatment to exit out of the outlet.

16. The therapeutic scalp care tool of claim 10 further comprising a second flow control device which modifies the flow of the treatment out of the outlet.

17. The therapeutic scalp care tool of claim 16, wherein the second flow control device comprises a ball located in a socket within the applicator and the ball is operable to rotate freely within the socket allowing the treatment to escape around the ball as the ball rotates.

18. The therapeutic scalp care tool of claim 1 further comprising a removable reservoir positioned within the interior cavity of the body, wherein the removable reservoir is in fluid communication with the outlet and the treatment is located within the removable reservoir.

19. A method for treating an ailment on a scalp of a user, the method comprising
obtaining a treatment tool including
a body having a first end and a second end and an exterior wall defining an interior cavity and suitable to be held in a user's hand;
a treatment located within the interior cavity and operable to provide a therapeutic benefit to a person's scalp;
a flow control operable to contain the treatment within the interior cavity and release the treatment from the interior cavity through a passage in response to actuation of the flow control;
an applicator on the first end of the body in fluid communication with the flow control and having a single tip defining an outlet within a distal surface of the single tip in fluid communication with the passage, wherein the distal surface of the single tip is configured to contact the person's scalp and forms a rounded point sized to fit between a part or rows of hair to provide itch relief without cutting the person's scalp; and
a cap at the second end of the body, wherein
the cap is configured to removably attach to the second end of the body and close a filling aperture in the second end of the body open to the interior cavity,
the filling aperture is operable to fill the interior cavity,
the cap includes a second tip that does not include a fluid outlet, and
the cap is formed as a solid body or a sealed hollow body including an engagement end configured to seal the filling aperture and an exterior surface forming an exterior of the therapeutic scalp care tool;
applying the single tip to the person's scalp;
actuating the flow control to release the treatment to the person's scalp through the outlet; and
relieving the ailment by massaging an area occupied by the ailment with the single tip of the treatment tool and the treatment.

* * * * *